United States Patent [19]

Burress

[11] Patent Number: 4,469,908

[45] Date of Patent: Sep. 4, 1984

[54] ALKYLATION OF AROMATIC HYDROCARBONS

[75] Inventor: George T. Burress, Bridgewater, N.J.

[73] Assignee: Mobil Oil Corporation, New York, N.Y.

[21] Appl. No.: 429,600

[22] Filed: Sep. 30, 1982

Related U.S. Application Data

[63] Continuation of Ser. No. 969,630, Dec. 14, 1978, abandoned.

[51] Int. Cl.$^3$ .............................................. C07C 63/34
[52] U.S. Cl. ..................................................... 585/467
[58] Field of Search ............................. 585/487, 467; 252/455 Z; 423/328

[56] References Cited

U.S. PATENT DOCUMENTS

| | | | |
|---|---|---|---|
| 3,251,897 | 5/1966 | Wise | 260/671 |
| 3,385,906 | 5/1968 | Kaufman | 260/671 |
| 3,751,506 | 8/1973 | Burress | 260/671 R |
| 3,755,483 | 8/1973 | Burress | 260/671 R |
| 4,049,737 | 9/1977 | Dwyer et al. | 260/671 P |
| 4,291,185 | 9/1981 | Kaeding | 585/467 |

OTHER PUBLICATIONS

Kirk-Othmer, *Encyclopedia of Chemical Technology*, 3rd Ed., vol. 2, pp. 58–65.
March, Jerry, *Advanced Organic Chemistry:* Reactions, Mechanisms, and Structure, N.Y., McGraw-Hill, 1968, pp. 406–413.
Morrison and Boyd, *Organic Chemistry*, 2d Ed., pp. 345–346 and 359–361.

*Primary Examiner*—Richard Raymond
*Assistant Examiner*—Raymond Covington
*Attorney, Agent, or Firm*—A. J. McKillop; M. G. Gilman; E. F. Kenehan, Jr.

[57] ABSTRACT

A process for the alkylation of aromatic hydrocarbons with alkylating agents having from one to five, and preferably three to five, carbon atoms. The reactants are brought into contact, preferably in the liquid phase, in the presence of a crystalline zeolite catalyst characterized by a silica to alumina ratio of at least 12 and a constraint index within the approximate range of 1–12. The reaction is conducted at 100° C. to 300° C. and a pressure of from about $10^5$ N/m$^2$ to about $2 \times 10^7$ N/m$^2$.

2 Claims, No Drawings

ALKYLATION OF AROMATIC HYDROCARBONS

This is a continuation of application Ser. No. 969,630 filed Dec. 14, 1978, now abandoned.

BACKGROUND OF THE INVENTION

1. Field of the Invention

This invention is directed to the catalytic alkylation of aromatic hydrocarbon molecules and is particularly concerned with a process for liquid-phase alkylation.

2. Description of the Prior Art

Alkylation is one of the most important and useful reactions of hydrocarbons. Lewis and Bronsted acids, including a variety of natural and synthetic zeolites, have been used as catalysts. Alkylation of aromatic hydrocarbon compounds employing certain crystalline zeolite catalysts is known in the art. For instance, U.S. Pat. No. 3,251,897 describes liquid phase alkylation in the presence of crystalline aluminosilicates such as faujasite, heulandite, clinoptilolite, mordenite, dachiardite, zeolite X and zeolite Y. The temperature of such alkylation procedure does not exceed 600° F., thereby maintaining patentee's preferable operating phase as substantially liquid.

Also, U.S. Pat. No. 2,904,607 shows alkylation of hydrocarbon compounds in the presence of certain crystalline zeolites. The zeolites described for use in this patent are crystalline metallic aluminosilicates, such as, for example, magnesium aluminosilicate.

U.S. Pat. Nos. 3,631,120 and 3,641,177 describe liquid phase processes for alkylation of aromatic hydrocarbons with olefins in the presence of certain zeolites. U.S. Pat. No. 3,631,120 discloses use of an ammonium exchanged, calcined zeolite having a silica to alumina mole ratio of between 4.0 and 4.9. U.S. Pat. No. 3,641,177 discloses use of a zeolite catalyst activated in a particular manner.

Unfortunately, when propylene and higher molecular weight olefins were used for alkylation in the presence of zeolite ZSM-5, side reactions such as dealkylation and so forth take place and usually significantly reduced the selectivity to desired products.

U.S. Pat. No. 3,755,483 disclosed that the vapor phase reaction of propylene with benzene and toluene, in the presence of zeolite ZSM-12, gave high activity and high selectivity to produce isopropylbenzene and isopropylmethylbenzene. However, the process necessitated operation in the vapor phase with relatively high temperatures and pressures, thereby promoting dealkylation and olefin decomposition which was especially evident when the alkylating agent comprised an olefin of three or more carbon atoms.

SUMMARY OF THE INVENTION

A process has now been discovered whereby aromatic hydrocarbons, containing both polar and nonpolar substituents, may be successfully alkylated with olefins and with alcohols containing from one to five carbon atoms. Surprising and substantial increases in product yield, conversion and selectivity are obtained by operating at lower temperatures than heretofore and essentially in the liquid phase. This increase is especially evident for the use of alkylating agents of three or more carbon atoms where higher temperatures promote dealkylation and olefin decomposition.

The reaction is carried out at temperatures of between about 100° C. and about 300° C., and preferably from about 200° C. to about 250° C., in the presence of a specific type of crystalline zeolite catalyst, such zeolite catalyst being characterized by having a silica to alumina ratio of at least about 12 and a constraint index, as hereinafter defined, within the approximate range of 1 to 12. The catalyst particularly useful in this invention is the zeolite ZSM-12.

DESCRIPTION OF SPECIFIC EMBODIMENTS

The crystalline zeolites utilized herein are members of a novel class of zeolites that exhibits unusual properties. Although these zeolites have unusually low alumina contents, i.e. high silica to alumina ratios, they are very active even when the silica to alumina ratio exceeds 30. The activity is surprising since catalytic activity is generally attributed to framework aluminum atoms and/or cations associated with these aluminum atoms. These zeolites retain their crystallinity for long periods in spite of the presence of stream at high temperature which induces irreversible collapse of the framework of other zeolites, e.g. of the X and A type. Furthermore, carbonaceous deposits, when formed, may be removed by controlled burning at higher than usual temperatures to restore activity. These zeolites, used as catalysts, generally have low coke-forming activity and therefore are conducive to long times on stream between regenerations by burning with oxygen-containing gas such as air.

An important characteristic of the crystal structure of this class of zeolites is that it provides constrained access to and egress from the intracrystalline free space by virtue of having an effective pore size intermediate between the small pore Linde A and the large pore Linde X, i.e. the pore windows of the structure have about a size such as would be provided by 10-membered rings of silicon and aluminum atoms interconnected by oxygen atoms. It is to be understood, of course, that these rings are those formed by the regular disposition of the tetrahedra making up the anionic framework of the crystalline zeolite, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the intracrystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e. they exhibit "hydrophobic" properties. It is believed that this hydrophobic character is advantageous in the present invention.

The zeolites useful in this invention have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than hexane is excluded and the zeolite is not of the desired type. Windows of 10 membered rings are preferred, although in some instances excessive puckering of the rings or pore blockage may render these zeolites ineffective.

Twelve-membered rings usually do not offer sufficient constraint to produce the advantageous conversions, although the puckered 12-ring structure of TMA offretite shows constrained access. Other 12-ring structures may exist which may be operative.

Rather than attempt to judge from crystal structure whether or not a zeolite possesses the necessary constrained access to molecules larger than normal paraffins, a simple determination of the "Constraint Index" as herein defined may be made by passing continuously a mixture of an equal weight of hexane and 3-methylpentane over a small sample, approximately one gram or less, of the zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature adjusted between 290° C. and 510° C. to give an overall conversion between 10% and 60%. The mixture of hydrocarbons is passed at 1 liquid hourly space velocity (i.e. 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical zeolites are:

| ZEOLITE | C.I. |
| --- | --- |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| TMA Offretite | 3.7 |
| Beta | 0.6 |
| ZSM-4 | 0.5 |
| H—Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby have different Constraint Indexes. Constraint Index seems to vary somewhat with severity of operation (conversion) and the presence or absence of binders. Therefore, it will be appreciated that it may be possible to so select test conditions to establish more than one value in the range of 1 to 12 for the Constraint Index of a particular zeolite. Such a zeolite exhibits the constrained access as herein defined and is to be regarded as having a Constraint Index of 1 to 12. Also contemplated herein as having a Constraint Index of 1 to 12 and therefore within the scope of the novel class of highly siliceous zeolites are those zeolites which, when tested under two or more sets of conditions within the above specified ranges of temperature and conversion, produce a value of the Constraint Index slightly less than 1, e.g. 0.9, or somewhat greater than 12, e.g. 14 or 15, with at least one other value of 1 to 12. Thus, it should be understood that the Constraint Index value as used herein is an inclusive rather than an exclusive value. That is, a zeolite when tested by any combination of conditions within the testing definition set forth hereinabove to have a Constraint Index of 1 to 12 is intended to be included in the instant catalyst definition regardless that the same identical zeolite tested under other defined conditions may give a Constraint Index value outside of 1 to 12.

The class of zeolites defined herein is exemplified by ZSM-5, ZSM-11, ZSM-12, ZSM-23, ZSM-35, ZSM-38, and other similar materials. U.S. Pat. No. 3,702,886 describing and claiming ZSM-5 is incorporated herein by reference.

ZSM-11 is more particularly described in U.S. Pat. No. 3,709,979, the entire content of which is incorporated herein by reference.

ZSM-12 is more particularly described in U.S. Pat. No. 3,832,449, the entire content of which is incorporated herein by reference.

ZSM-23 is more particularly described in U.S. Pat. No. 4,076,842, the entire content of which is incorporated herein by reference.

ZSM-35 is more particularly described in U.S. Pat. No. 4,016,245, the entire content of which is incorporated herein by reference.

ZSM-38 is more particularly described in U.S. Pat. No. 4,046,859, the entire content of which is incorporated herein by reference.

The specific zeolites described, when prepared in the presence of organic cations, are substantially catalytically inactive, possibly because the intracrystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air to about 540° C. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline zeolites are ZSM-5, ZSM-11, ZSM-12, ZSM-23, ZSM- 35, and ZSM-38, with ZSM-12 being particularly preferred.

In a preferred aspect of this invention, the zeolites hereof are selected as those having a crystal framework density, in the dry hydrogen form, of not less than about 1.6 grams per centimeter. It has been found that zeolites which satisfy all three of these criteria are most desired for several reasons. When hydrocarbon products or by-products are catalytically formed, for example, such zeolites tend to maximize the production of gasoline boiling range hydrocarbon products. Therefore, the preferred zeolites of this invention are those having a Constraint Index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g. on Page 19 of the article on Zeolite Structure by W. M. Meier. This paper, the entire contents of which are incorporated herein by reference, is included in "Proceedings of the Conference on Molecular Sieves, London, April 1967" published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space. It is possible that the unusual sustained activity and stability of this class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| ZSM-12 | | 1.8 |
| ZSM-23 | | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

In practicing the desired conversion process, it may be desirable to incorporate the above described crystalline zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix on an anhydrous basis may vary widely, with the zeolite content ranging from between about 1 to about 99 percent by weight and more usually in the range of about 5 to about 80 percent by weight of the dry composite.

Alkylation of aromatic hydrocarbon molecules in the presence of the above-described catalyst is effected by contact of the reactants at a temperature of between about 100° C. and about 300° C., and preferably between about 200° C. and about 250° C. The reaction generally takes place at atmospheric pressure, but the pressure may be within the approximate range of about 1 atmosphere to about 200 atmospheres. The molar ratio of aromatic hydrocarbon to alkylating agent employed is within the approximate range of 20/1 to 1/1. Reaction is suitably accomplished utilizing a feed weight hourly space velocity (WHSV) of between about 0.1 and about 100. The latter WHSV is based upon the total weight of active catalyst and binder therefor.

Exemplary of the hydrocarbons which may be alkylated by the process of this invention are aromatic compounds such as benzenes, naphthalenes, anthracenes, and the like and substituted derivatives thereof; and alkyl substituted aromatics, e.g. toluene, xylene, and homologs thereof. In addition, other non-polar substituent groups may also be attached to the aromatic ring, including by way of example:

Methyl ($-CH_3$)
Ethyl ($-C_2H_5$)
Tert-butyl ($-C(CH_3)_3$)
Alkyl ($-C_nH_{(2n+1)}$)
Cycloalkyl ($-C_nH_{(2n-1)}$)

Phenyl ($C_6H_7$) and
Aryl (any aromatic radical)

Aromatic hydrocarbons which may be alkylated by the present process likewise include those having polar substituents on the aromatic ring or on a side chain attached thereto. Non-limiting examples include phenol, cresols, halogenated aromatics and so forth.

In accordance with this invention, the preferred alkylating agents are olefins such as ethylene, propylene, dodecylene, and so on, as well as formaldehyde, alkyl halides and alcohols, the alkyl portion thereof preferably having from 1 to 24 carbon atoms. Numerous other acyclic compounds having at least one reactive alkyl radical may be utilized as alkylating agents.

The process of this invention may be carried out as a batch-type, semi-continuous or continuous operation utilizing a fixed, fluidized or moving bed catalyst system. A preferred embodiment entails use of a fluidized catalyst zone wherein the reactants, i.e. the aromatic hydrocarbon and alkylating agent are passed concurrently or countercurrently through a moving fuidized bed of the catalyst. The fluidized catalyst after use is conducted to a regeneration zone wherein coke is burned from the catalyst in an oxygen-containing atmosphere, e.g. air, at an elevated temperature, after which the regenerated catalyst is recycled to the conversion zone for further contact with the reactants. Subsequent to leaving the reaction zone, the desired products may be recovered from the reactor effluent, for instance by distillation, and the unreacted hydrocarbons recycled for reuse in the process.

The following examples will serve to illustrate the process of this invention without limiting the scope or utility thereof. The catalyst in all cases comprised 4.6 gms of ZSM-12 prepared as disclosed in U.S. Pat. No. 3,832,449 and consisted of 65 wt % HZSM-12 and 35 wt % $Al_2O_3$ binder. The reaction products were analyzed with a gas chromatograph equipped with a hot wire detector. Positive identification of the various compounds was made with GC/MS, IR, and/or NMR.

EXAMPLE 1

Benzene with Methanol

Benzene was alkylated with methanol at 250° C. and atmospheric pressure using HZSM-12 extrudate as catalyst. At this relatively low temperature 90% of the methanol was converted to benzene alkylation products. Table I shows the product selectivity and also the isomer distribution of the methylbenzenes that were produced.

Reactor temperatures from 200° C. to 300° C. were explored. Below about 240° C. there was a rapid decline in methanol conversion and at 200° C. the conversion was essentially zero. Above about 260° C. no additional alkylation products were formed.

The main alkylation products were toluene and xylenes. The xylene fraction, formed by alkylation of the toluene, amounted to 15% of the total product and was unusual in that the ortho isomer predominated. The actual isomer distribution was 47%-ortho, 40%-meta, 13%-para. Using unmodified HZSM-5 (U.S. Pat. No. 3,702,886) as catalyst and similar experimental conditions, the xylene isomer ratio was 22%-ortho, 54%-meta and 24%-para. Since the methylation of toluene is ortho directing it would appear that the initially formed ortho isomer is only partially isomerized by HZSM-12 whereas with HZSM-5 isomerization to equilibrium occurs.

TABLE 1

BENZENE ALKYLATION WITH METHANOL OVER HZSM-12

| FEED: | 7/1 BENZENE/METHANOL - MOLE/MOLE |
|---|---|
| TEMPERATURE: | 250° C. |
| PRESSURE: | ATMOSPHERIC |
| WHSV: | 5.8 BENZENE - 0.3 METHANOL |
| CONVERSION-WT %: | 10% BENZENE - >90% METHANOL |

| COMPOUND | WT % SELECTIVITY | ISOMER DISTRIBUTION |
|---|---|---|
| TOLUENE | 73.0% | — |
| XYLENES | 15.0% | PARA - 13.0% |
|  |  | META - 40.0% |
|  |  | ORTHO - 47.0% |
| $C_9$ | 4.5% | 1,3,5-TRIMETHYLBENZENE - 23.0% |
|  |  | 1,2,4-TRIMETHYLBENZENE - 67.0% |
|  |  | 1,2,3-TRIMETHYLBENZENE - 10.0% |
| $C_{10}$ | 4.5% | 1,2,3,4-TRIMETHYLBENZENE - 55.0% |
|  |  | 1,2,3,5-TRIMETHYLBENZENE - 37.0% |
|  |  | 1,2,3,4-TRIMETHYLBENZENE - 8.0% |
| $C_{11}$ | 3.5% | PENTAMETHYLBENZENE - 100.0% |
| $C_{11+}$ | 1.5% | HEXAMETHYLBENZENE - 40.0% |
|  |  | UNKNOWN - 60.0% |

EXAMPLES 2-5

Benzene with $C_3$-$C_5$ Olefins

Benzene was alkylated with $C_3$ through $C_5$ alkenes in the presence of HZSM-12, at various temperatures and pressures. The reactions are summarized in Table II.

TABLE II

BENZENE ALKYLATION OVER HZSM-12

| EXAMPLE | ALKYLATING AGENT | TEMP. °C. | PRESSURE | WHSV | BENZENE/ALKYLATING AGENT MOLE RATIO | % CONVERSION ALKYLATING AGENT | PRODUCTS-% SELECTIVITY |
|---|---|---|---|---|---|---|---|
| 1 | METHANOL | 250 | ATMOSPHERIC | 6 | 7/1 | >90 | TOLUENE-73% XYLENE-15% $C_9$-4.5% $C_9^+$-7.5% |
| 2 | PROPYLENE | 200 | 300 psig | 6 | 7/1 | >95 | ISOPROPYL BENZENE-92% DIISOPROPYL-BENZENE-7.5% |
| 3 | 1-BUTENE OR 2-BUTENE | 190 | 350 psig | 6 | 7/1 | >95 | SEC-BUTYL-BENZENE-95+% |
| 4 | ISOBUTYLENE | 190 | 350 psig | 6 | 7/1 | >95 | TERTIARY BUTYL-BENZENE- |

TABLE II-continued
BENZENE ALKYLATION OVER HZSM-12

| EX-AMPLE | ALKYLATING AGENT | TEMP. °C. | PRESSURE | WHSV | BENZENE/ALKYL-ATING AGENT MOLE RATIO | % CONVERSION ALKYLATING AGENT | PRODUCTS-% SELECTIVITY |
|---|---|---|---|---|---|---|---|
| 5 | 2-METHYL-BUTENE-90% 2-PENTENE-10% | 200 | 350 psig | 6 | 7/1 | >95 | 95+% TERTIARY PENTYL-BENZENE-52% 1,2-DIMETHYL PROPYL-BENZENE-38% |

The data illustrates the exceptional alkylation activity and selectivity of ZSM-12 catalyst at temperatures of 250° C. and below, particularly with respect to alkylating agents $C_3$ and higher.

EXAMPLE 6

Toluene with methanol

Toluene was alkylated with methanol in the presence of HZSM-12 catalyst at 250° C. and atmospheric pressure. The operating conditions and products formed are shown in Table III.

TABLE III
TOLUENE ALKYLATION WITH METHANOL OVER HZSM 12

| FEED: | 2.2/1 TOLUENE/METHANOL - MOLE RATIO |
|---|---|
| TEMPERATURE: | 250° C. |
| PRESSURE: | ATOMSPHERIC |
| WHSV: | 11.5 TOLUENE - 1.8 METHANOL |
| CONVERSION - WT%: | 28% TOLUENE - 70% METHANOL |

| COMPOUND | WT % SELECTIVITY | ISOMER DISTRIBUTION |
|---|---|---|
| XYLENES | 76.0 | PARA - 14.0% META - 25.0% ORTHO - 61.0% |
| $C_9$ | 16.0 | 1,3,5-TRIMETHYLBENZENE-3.0% 1,2,3-TRIMETHYLBENZENE-75.0% 1,2,3-TRIMETHYLBENZENE-22.0% |
| $C_9^+$ | 8.0 | |

EXAMPLE 7-10

Toluene alkylation with $C_2$-$C_4$ olefins

Toluene was alkylated with $C_2$ through $C_4$ olefins in the presence of HZSM-12 catalyst at a variety of temperatures and pressures. Table IV is a summary of the reaction conditions and products formed.

TABLE IV
TOLUENE ALKYLATION OVER HZSM-12

| EX-AMPLE | ALKYLATING AGENT | TEMP. °C. | PRESSURE | WHSV | TOLUENE/ALKYL-ATING AGENT MOLE RATIO | % CONVERSION ALKYLATING AGENT | PRODUCTS-% SELECTIVITY |
|---|---|---|---|---|---|---|---|
| 6 | METHANOL | 250 | ATMOSPHERIC | 11 | 2.2/1 | 70 | XYLENES-76% (61% ORTHO 25% META 14% PARA) $C_9$-16% $C_9^+$-8% |
| 7 | ETHYLENE | 300 | ATMOSPHERIC | 6 | 7/1 | 60 | ETHYLTOLUENE 90% (40% ORTHO 38% META 22% PARA) |
| 8 | PROPYLENE | 250 | 500 psig | 6 | 7/1 | >95 | ISOPROPYL-TOLUENE-95% (32% PARA 62% META 6% ORTHO) |
| 9 | 1-BUTENE or 2-BUTENE | 200 | 300 psig | 6 | 7/1 | >95 | SECONDARY BUTYLTOLUENE 95% (60% PARA 40% META) |
| 10 | ISOBUTYLENE | 190 | 300 psig | 6 | 7/1 | >95 | TERTIARY BUTYLTOLUENE 95% (60% PARA, 35% |

TABLE IV-continued
TOLUENE ALKYLATION OVER HZSM-12

| EX-AMPLE | ALKYLATING AGENT | TEMP. °C. | PRESSURE | WHSV | TOLUENE/ALKYL-ATING AGENT MOLE RATIO | % CONVERSION ALKYLATING AGENT | PRODUCTS-% SELECTIVITY |
|---|---|---|---|---|---|---|---|
| | | | | | | | META) |

Toluene alkylation differs from benzene alkylation in that the initial alkylation product consists of isomers. Although the reactions with toluene can be made at the same temperatures as benzene, it was found necessary to vary the temperature in order to optimize the formation of a desired isomer. This is illustrated in Example 11 with toluene-propylene.

EXAMPLE 11

Cymene (isopropyltoluene), the product of toluene-propylene alkylation, is of commercial interest as a large volume chemical intermediate for cresol manufacture. Of the three isomers, meta cymene has the greatest potential value and ortho cymene the least value. Because of the high potential for immediate commercial application, the reaction parameters of toluene-propylene alkylation with HZSM-12 were studied in depth to optimize meta cymene production.

The variable that most affected selectivity to meta cymene was found to be temperature. This is illustrated in the following Table V:

TABLE V
TOLUENE-PROPYLENE ALKYLATION HZSM-12 CATALYST

| | Isopropyltoluene Isomer Distribution | | |
|---|---|---|---|
| Temp. °C. | Ortho | Meta | Para |
| 200 | 18.4% | 31.8% | 49.8% |
| 230 | 6.9% | 60.3% | 32.8% |
| 260 | 5.3% | 63.7% | 31.0% |

WHSV - 5.7 Toluene/0.4 C$_3$H$_6$
Pressure - 500 psig
Molar Feed Ratio - 6.25/1 Toluene/C$_3$H$_6$ Increasing the temperature above 260° C. did not give a higher meta cymene content.

Propylene conversion at 230°–240° C. averaged 90–95% during a 5 day run. The only indication of a decrease in catalyst activity was a change in isomer distribution versus time on stream. This was denoted by a decrease in the meta isomer and an increase in the para and ortho isomers.

EXAMPLES 12–15

Ethylbenzene alkylation

Alkylation of ethylbenzene with methanol, propylene, butenes and isobutylene, respectively, in the present of ZSM-12 catalyst, is summarized in Table VI.

TABLE VI
ETHYLBENZENE ALKYLATION OVER HZSM-12

| EX-AMPLE | ALKYLATING AGENT | TEMP. °C. | PRESSURE | WHSV | ETHYL-BENZENE/ALKYL-ATING AGENT MOLE/RATIO | % CONVERSION AGENT | PRODUCTS-% SELECTIVITY |
|---|---|---|---|---|---|---|---|
| 12 | METHANOL | 200 | ATMOSPHERIC | 6 | 3.5/1 | 55 | BENZENE-12% TOLUENE-4% ETHYL-TOLUENE-64% (47% ORTHO 34% META 19% PARA) C$_9$+-20% |
| 13 | PROPYLENE | 200 | ATMOSPHERIC | 11 | 7/1 | >95 | ISOPROPYL ETHYLBENZENE 90% (41% PARA 59% META, ORTHO |
| 14 | 1-BUTENE or 2-BUTENE | 200 | 300 psig | 6 | 7/1 | >95 | SECONDARY BUTYLETHYL-BENZENE-90% (60% PARA, 40% META) |
| 15 | ISOBUTYLENE | 200 | 300 psig | 6 | 7/1 | >95 | TERTIARY BUTYLETHYL-BENZENE-90% (90% PARA, 10% META) |

Alkylation of ethylbenzene with methanol using HZSM-12 as catalyst was studied to determine if para-ethyltoluene could be selectively produced. As can be seen in Table VI, selectivity for total ethyltoluene was 64%. Of this 64% the isomer ratio was 47% ortho, 34% meta and 19% para. This isomer distribution is similar to that obtained by alkylating toluene with ethylene over HZSM-12.

The alkylation of ethylbenzene with propylene was found to proceed smoothly at 200° C. at atmospheric pressure. Propylene conversion was >95% and the selectivity to isopropylethylbenzene was 90%.

Operating in the liquid phase, butene conversion was >95% with 90% selectivity to butylethylbenzene. 1-butene or 2-butene alkylated to produce secondary butylethylbenzene. The isomer ratio was 60% para and 40% meta at the temperature used for the experiment. No ortho isomer was found.

At the same operating conditions, isobutylene alkylated to give identical olefin conversion and selectivity to product as was found with 1-butene or 2-butene. The isomer ratio of the tertiary butylethylbenzene was 90% para and 10% meta. This ratio is close to the 92/8 ratio obtained with conventional Freidel-Kraft catalysts, but conversion and selectivity are higher with HZSM-12.

EXAMPLES 16-19

Isopropylbenzene alkylation

The alkylation of isopropylbenzene over HZSM-12 is summarized in Table VII.

price could be substantially reduced. Because of this the alkylation reaction parameters of isopropylbenzene-propylene were studied to determine if the meta isomer could be selectively produced.

At 200° C. and atmospheric pressure, the meta/para ratio was 40/60 as shown in Table VII. Increasing the reactor temperature to 235° C. reversed this and the meta/para ratio became 61/39. A further increase in the temperature did not improve the meta/para ratio beyond 61/39. The ortho isomer was not found. However, this is a difficult chromatographic analysis and it is possible 2-3% could have gone undetected.

Cumene (isopropylbenzene) can be alkylated with butenes at 200° C. The reaction must be carried out in the liquid phase to prevent catalyst deactivation. Conversion of the olefins was >95% with 95% selectivity. The 1- and 2-butenes alkylated to produce secondary butylcumene and isobutylene gave tertiary butylcumene.

EXAMPLE 20

Xylene alkylation with methanol

Experimentally the alkylation of xylene with methanol was limited to the ortho isomer because only two

TABLE VII

ISOPROPYLBENZENE ALKYLATION OVER HZSM-12

| | ALKYLATING AGENT | TEMP °C. | PRESSURE | WHSV | ISOPROPYLBENZENE/ ALKYLATING AGENT MOLE RATIO | % CONVERSION ALKYLATING AGENT | PRODUCTS-% SELECTIVITY |
|---|---|---|---|---|---|---|---|
| 16 | METHANOL | 200 | ATMOSPHERIC | 11 | 3.5/1 | 30 | BENZENE-26% TOLUENE-6% DIISOPROPYL-BENZENE-41% ISOPROPYL-BENZENE-20% $C_{10}{}^+$-9% |
| 17 | PROPYLENE | 200 | ATMOSPHERIC | 11 | 7/1 | >95 | DIISOPROPYL-BENZENE-95% (60% PARA, 40% META) |
| 18 | 1-BUTENE or 2-BUTENE | 200 | 300 psig | 6 | 7/1 | >95 | SECONDARY BUTYL ISO-PROPYLBEN-ZENE-95% (75% PARA, 25% META) |
| 19 | ISOBUTYLENE | 200 | 300 psig | 6 | 7/1 | >95 | TERTIARY BUTYL ISO-PROPYL-BENZENE (95% PARA) |

Isopropylbenzene could not be selectively alkylated with methanol to form isopropyltoluene. At 200° C. disproportionation of the isopropylbenzene was the predominate reaction. The product was 41% diisopropylbenzene, 24% benzene and 20% isopropyltoluene. Part of the benzene was alkylated as shown by the presence of 6% toluene.

The meta or para isomers of diisopropylbenzene can be oxidized to the corresponding dihydroperoxides and subsequently rearranged with an acid catalyst to make resorcinol, hydroquinone and acetone. Resorcinol has the potential of becoming a large volume chemical for use in thermosetting plywood laminates if the selling trimethylbenzene isomers should be formed, assuming an absence of isomerization. These are: 1,2,3,- and 1,2,4-trimethylbenzene. Any 1,3,5-isomer would require an isomerization step.

Table IX lists reaction parameters and isomer distribution for the experiment. Using a 1/1 molar ratio of o-xylene/methanol the ratio of 1,2,3- to 1,2,4-isomer was 1/1. Only 2% of the 1,3,5-isomer was present. With the conditions of this experiment, little isomerization of either the o-xylene or the trimethylbenzenes occurred. Increasing the reactor temperature to 350° C. resulted in an almost equilibrium mixture of the alkylation products.

TABLE IX

ORTHO XYLENE ALKYLATION WITH METHANOL OVER HZSM-12

| FEED: | 1/1 o-xylene/Methanol Mole Ratio |
|---|---|
| TEMPERATURE: | 300° C. |
| PRESSURE: | Atmospheric |
| WHSV: | 10.0 o-xylene - 1.7 Methanol |
| CONVERSION: | 18% o-xylene - 60% Methanol |

| COMPOUND | WT % SELECTIVITY OF LIQUID PRODUCT | ISOMER DISTRIBUTION |
|---|---|---|
| $C_9$ | 62.4 | 1,3,5-TRIMETHYLBENZENE-2.0% <br> 1,2,4-TRIMETHYLBENZENE-49.0% <br> 1,2,3-TRIMETHYLBENZENE-49.0% |
| $C_{10}$ | 24.0 | 1,2,4,5-TETRAMETHYLBENZENE-82.0% <br> 1,2,3,5-TETRAMETHYLBENZENE-16.0% <br> 1,2,3,4-TETRAMETHYLBENZENE-2.0% |
| $C_{10}+$ | 13.6 | |

EXAMPLE 21-23

Xylene alkylation with olefins ortho-Xylene was alkylated with $C_3$ and $C_4$ olefins over HZSM-12 at 190°–200° C. The reaction conditions and products are given in Table X.

The experimental conditions and product selectivity for xylene-butene alkylation experiments are shown in Table X. With the indicated reaction conditions only ortho-xylene could be appreciably alkylated.

EXAMPLE 22

TABLE X

ORTHO-XYLENE ALKYLATION OVER HZSM-12

| EXAMPLE | ALKYLATING AGENT | TEMP. °C. | PRESSURE | WHSV | XYLENE/ALKYLATING AGENT MOLE RATIO | % CONVERSION ALKYLATING AGENT | PRODUCTS-% SELECTIVITY |
|---|---|---|---|---|---|---|---|
| 20 | METHANOL | 300 | ATMOSPHERIC | 12 | 1/1 | 60 | $C_9$-62% <br> $C_{10}$-24% <br> $C_{10}+$-14% |
| 21 | PROPYLENE | 200 | ATMOSPHERIC | 6 | 7/1 | >90 | 1,2-DIMETHYL-4-ISOPROPYLBENZENE 93% <br> 1,2-DIMETHYL-3-ISOPROPYLBENZENE 7% |
| 22 | 1-BUTENE or 2-BUTENE | 200 | 300 psig | 6 | 7/1 | 95 | 1,2-DIMETHYL-4-sec BUTYLBENZENE 96% |
| 23 | ISOBUTYLENE | 190 | 300 psig | 6 | 7/1 | 95 | 1,2-DIMETHYL-4-t BUTYLBENZENE 97% |

EXAMPLE 21

Xylene-Propylene

The xylenes were reacted with propylene at atmospheric pressure and temperatures varying from 200°–250° C. Under these conditions only ortho-xylene gave a significant alkylation product. These results are not consistent with published relative alkylation rates of the xylene isomers and propylene. Operating in the liquid phase with a low WHSV might induce alkylation with all isomers.

The two major alkylation products formed from o-xylene and propylene were 1,2-dimethyl-4-isopropylbenzene and 1,2-dimethyl-3-isopropylbenzene. The ratio of these compounds was 93/7. Using a liquid catalyst of $BF_3$—$H_3PO_4$ it has been reported these compounds were found in a ratio of 96/4.

During the experiments with o-xylene essentially no isomerization of the xylene was noted. With meta and para xylenes as the temperatures was increased to force alkylation, isomerization occurred and the only alkylation product was that associated with o-xylene.

ortho-Xylene—1-Butene or 2-Butene

At 200° C. and 300 psig o-xylene was alkylated with 1-butene or 2-butene to make 1,2-dimethyl-4-sec-butylbenzene with 96% selectivity. Conversion of the olefin was 95%.

EXAMPLE 23 ortho-Xylene-Isobutylene

At 190° C. o-xylene was alkylated with isobutylene to give 1,2-dimethyl-4-t-butylbenzene. The selectivity was 97% and conversion of the olefin 95%. The reaction was maintained for 48 hours without a decline in catalyst activity.

EXAMPLES 24-26

Alkylation of Chlorobenzene

Halogenated aromatics are difficult to alkylate because of the deactivating effect of the halogen upon the aromatic ring. However, using HZSM-12 as catalyst it was possible to non-selectively alkylate chlorobenzene with methanol or ethylene. The results are shown in Table XI. In each instance, the ortho isomer is the major product.

TABLE XI
CHLOROBENZENE ALKYLATION OVER HZSM-12

| EXAMPLE | ALKYLATING AGENT | TEMP. °C. | PRESSURE | WHSV | CHLOROBENZENE ALKYLATING AGENT MOLE/RATIO | % CONVERSION ALKYLATING AGENT | PRODUCTS-% SELECTIVITY |
|---|---|---|---|---|---|---|---|
| 24 | METHANOL | 275 | ATMOSPHERIC | 6 | 7/1 | 65 | CHLOROTOLUENE-70% (20% PARA 20% META 60% ORTHO) |
| 25 | ETHYLENE | 325 | ATMOSPHERIC | 6 | 7/1 | 50 | ETHYLCHLOROBENZENE-80% (24% PARA 20% META 56% ORTHO) |
| 26 | PROPYLENE | 250 | 300 | 6 | 10.6/1 | 99 | ISOPROPYLCHLOROBENZENE 99% (60% PARA 20% META 20% ORTHO) |

EXAMPLE 26
Chlorobenzene-Propylene

The results shown in Table XII were obtained using propylene as the alkylating agent and operating in the liquid phase. This reaction was exceptional because 95% of the propylene was converted to isopropylchlorobenzene with a selectivity of 99%. This compares to published data which indicate aluminosilicate or $H_2SO_4$ catalysts gave approximately 85% conversion of the propylene. In the case of $H_2SO_4$, the published isomer distribution was 80%-ortho, 20%-para. The meta isomer was not found. With HZSM-12 as catalyst the isomer ratio was 60%-para, 20%-meta, 20%-ortho.

TABLE XII
EXAMPLE 26
CHLOROBENZENE
ALKYLATION WITH PROPYLENE

| Temperature - | 250° C. |
|---|---|
| Pressure - | 250 psig |
| WHSV chlorobenzene/propylene | 8.1/0.25 |
| Chlorobenzene/propylene - | Mole/mole 10.6/1 |

| Reactor Effluent | Wt. % | Selectivity, % |
|---|---|---|
| Lt. Ends | 0.19 | 1.59% |
| Chlorobenzene | 88.05 | — |
| Ortho chlorocumene | 2.14 | 17.91% |
| Meta chlorocumene | 2.39 | 20.00% |
| Para chlorocumene | 7.22 | 60.42% |
| Other | Trace | |
| Feed-Wt. %: Chlorobenzene-96.6% | | Propylene-3.4% |

Table XIII summarizes the results of Examples 1 through 26, listing the aromatics versus alkylating agent used. Plus and minus signs are used to qualitatively indicate, in a very general sense, the activity and selectivity obtained.

TABLE XIII
ALKYLATION WITH HZSM-12 ZEOLITE

| EXAMPLES | AROMATIC | OLEFIN | | | | |
|---|---|---|---|---|---|---|
| | | $C_1{}^a$ | $C_2$ | $C_3$ | $C_4$ | $C_5$ |
| 1–5 | BENZENE | + | + | +++ | +++ | +++ |
| 6–11 | TOLUENE | + | + | +++ | +++ | — |
| 12–15 | ETHYLBENZENE | — | — | +++ | +++ | — |
| 16–19 | ISOPROPYLBENZENE | — | — | +++ | +++ | — |
| 20–23 | o-XYLENE | + | — | +++ | +++ | — |
| 24–26 | CHLOROBENZENE | + | + | +++ | — | — |

$^a$Alcohol only

From the foregoing it will be abundantly apparent to those skilled in the art that ZSM-12 zeolite has exceptional alkylation activity and selectivity with respect to aromatic molecules, particularly with $C_3$ and higher olefins at temperatures of approximately 200°–250° C. It is shown to be selective for ethylation reactions, but overall conversions are lower than those encountered with ZSM-5 catalyst.

EXAMPLE 27
Temperature effect

Benzene was alkylated with propylene in the presence of HZSM-12 catalyst to show the effect of temperature on the reaction. Keeping the benzene/propylene feed and the pressure substantially constant, the reactor temperature was varied from 100°–300° C. and the reaction products analyzed for changes in composition. The parameters and results are given in Table XIV.

TABLE XIV
ALKYLATION OF BENZENE WITH PROPYLENE TO PRODUCE ISOPROPYLBENZENE
EFFECT OF TEMPERATURE

| Temperature, °C. | 100 | 125 | 150 | 175 | 200 | 200 | 115 | 150 | 275 | 300 |
|---|---|---|---|---|---|---|---|---|---|---|
| Pressure, psig | 300 | 300 | 300 | 300 | 300 | 300 | 300 | 300 | 300 | 300 |
| WHSV Benzene | 15.2 | 15.2 | 15.3 | 15.2 | 15.2 | 18.8 | 18.8 | 18.8 | 18.8 | 18.8 |
| WHSV Propylene | 1.2 | 1.2 | 1.2 | 1.2 | 1.2 | 2.4 | 2.4 | 2.4 | 2.4 | 2.4 |
| Mole Ratio: Benzene/Propylene | 6.7 | 6.7 | 6.7 | 6.7 | 6.7 | 6.7 | 6.7 | 6.7 | 6.7 | 6.7 |
| % Conversion Benzene | 0.9 | 7.1 | 12.0 | 10.4 | 11.8 | 11.3 | 11.3 | 12.2 | 12.3 | 12.1 |
| % Conversion Propylene | 14.9 | 59.0 | 97.9 | 98.4 | 98.1 | 98.1 | 99.4 | 98.1 | 98.0 | 97.8 |
| para-diisopropylbenzene | — | 100 | 100 | 100 | 67.0 | 72.2 | 55.4 | 32.6 | 31.9 | 29.8 |
| Selectivity to isopropylbenzene | 86.04 | 92.23 | 97.06 | 97.64 | 96.99 | 95.74 | 94.92 | 93.20 | 91.46 | 85.89 |
| m + p diisopropylbenzene | — | 2.92 | 2.67 | 2.06 | 2.70 | 3.96 | 4.54 | 5.56 | 4.96 | 3.75 |
| n-propylbenzene | 0 | 0 | 0 | 0 | 0 | 0 | .17 | .89 | 3.22 | 9.99 |

TABLE XIV-continued
ALKYLATION OF BENZENE WITH PROPYLENE TO PRODUCE ISOPROPYLBENZENE
EFFECT OF TEMPERATURE

| Material Balance | 97.5 | 97.8 | 98.2 | 96.5 | 96.6 | 100.2 | 99.6 | 98.0 | 98.1 | 97.9 |

EXAMPLE 28

Pressure effect

As in Example 27, benzene was again alkylated with propylene over ZSM-12 to produce isopropylbenzene, this time maintaining the temperature at 200° C. and varying the pressure from 0 to 500 psig. The results are shown in Table XV.

TABLE XVII
BENZENE ALKYLATION WITH ISOBUTYLENE-LIQUID PHASE

| | |
|---|---|
| Feed: | 8.6/1 Benzene/Isobutylene - mole/mole |
| Temperature: | 185° C. |
| Pressure: | 345 psig |
| WHSV: | 9.2 Benzene 0.8 Isobutylene |
| Conversion, Wt. % | 10.9% Benzene 91.0% Isobutylene |
| Component | Wt. % In Effluent |

TABLE XV
ALKYLATION OF BENZENE WITH PROPYLENE TO PRODUCE ISOPROPYLBENZENE EFFECT OF PRESSURE

| | | | | | | | | | | | | | | | | |
|---|---|---|---|---|---|---|---|---|---|---|---|---|---|---|---|---|
| Temperature, °C. | 200 | 200 | 200 | 200 | 200 | 200 | 200 | 200 | 200 | 200 | 200 | 200 | 200 | 200 | 200 | 200 |
| Pressure, psig | 0 | 25 | 50 | 75 | 100 | 125 | 100 | 150 | 200 | 250 | 300 | 350 | 200 | 300 | 400 | 500 |
| WHSV Benzene | 31.0 | 31.0 | 31.0 | 31.0 | 31.0 | 31.0 | 30 | 30 | 30 | 30 | 30 | 30 | 15.4 | 15.4 | 15.4 | 15.4 |
| WHSV Propylene | 1.8 | 1.8 | 1.8 | 1.8 | 1.8 | 1.8 | 2.4 | 2.4 | 2.4 | 2.4 | 2.4 | 2.4 | 1.2 | 1.2 | 1.2 | 1.2 |
| Mole Ratio: Benzene/Propylene | 9.5 | 9.5 | 9.5 | 9.5 | 9.5 | 9.5 | 6.6 | 6.6 | 6.6 | 6.6 | 6.6 | 6.6 | 6.8 | 6.8 | 6.8 | 6.8 |
| % Conversion Benzene | 8.4 | 9.5 | 9.6 | 10.3 | 10.3 | 10.3 | 14.0 | 14.3 | 14.1 | 13.7 | 13.1 | 14.0 | 10.8 | 11.8 | 9.3 | 13.3 |
| % Conversion Propylene | 92.6 | 97.0 | 97.5 | 94.8 | 95.1 | 94.8 | 97.9 | 95.4 | 96.8 | 97.1 | 95.7 | 46.8 | 98.3 | 48.1 | 87.7 | 97.9 |
| para-diisoproplybenzene in total DIPB | 67 | 68 | 71 | 77 | 78 | 77 | 66 | 76 | 81 | 81 | 86 | 9 | 78 | 67 | 100 | 80 |
| Selectivity to Isopropylbenzene | 83.8 | 86.8 | 88.6 | 88.5 | 89.8 | 90.4 | 88.5 | 90.3 | 94.0 | 94.8 | 96.3 | 96.7 | 95.7 | 97.0 | 97.9 | 96.4 |
| Material Balance | 101.6 | 101.4 | 102.6 | 100.5 | 99.7 | 99.7 | 99.1 | 102.4 | 98.3 | 99.6 | 100.0 | 99.1 | 97.1 | 96.6 | 97.2 | 99.6 |

| | |
|---|---|
| Light Ends | 0.7 |
| Benzene | 82.2 |
| C<sub>8</sub> | 0.1 |
| Tertiary butylbenzene | 16.7 |
| Sec. butylbenzene | 0.3 |

EXAMPLE 29

Vapor phase alkylation

Benzene was alkylated with isobutylene in the vapor phase with HZSM-12 catalyst at 190° C. and atmospheric pressure. The reaction is summarized in Table XVI.

TABLE XVI
BENZENE ALKYLATION WITH ISOBUTYLENE-VAPOR PHASE

| | |
|---|---|
| Feed: | 10.1/1 Benzene/Isobutylene - mole/mole |
| Temperature: | 190 ° C. |
| Pressure: | Atmospheric |
| WHSV | 11.7 Benzene 0.8 Isobutylene |
| Conversion, Wt. % | 3.4% Benzene 39% Isobutylene |
| Component | Wt. % In Effluent |
| Light Ends | 4.0 |
| Benzene | 90.2 |
| C$_8$ | 0.1 |
| Tertiary butylbenzene | 5.1 |
| Sec butylbenzene | 0.5 |
| C$_{10+}$ | 0.1 |

EXAMPLE 30 cl Liquid phase alkylation

Using the same reactants and catalyst as Example 29, the alkylation was carried out in the liquid phase by increasing the pressure to 345 psig. The results are shown in Table XVII.

A comparison of Example 29 (vapor phase) with Example 30 (liquid phase) will serve to demonstrate the surprising and substantial increase in conversion of reactants and selectivity to desired reaction products encountered by alkylating an aromatic molecule in the liquid phase at low temperature and in the presence of ZSM-12 catalyst.

It is to be understood that the foregoing description is merely illustrative of preferred embodiments of the hereindisclosed invention. Many variations thereon may be made by those skilled in the art without departing from the spirit of disclosed inventon and are intended to fall within the scope of the following claims.

What is claimed is:

1. A process for the alkylation of aromatic hydrocarbon compounds comprising contacting the aromatic hydrocarbon with isobutylene in the presence of a crystalline zeolite alkylation catalyst, at a temperature of between about 100° C. and about 300° C., said zeolite alkylation catalyst comprising zeolite ZSM-12, said process being carried out under sufficient pressure to maintain the organic reactants in the liquid phase when brought into contact with said zeolite catalyst, said pressure being between about $10^5 N/m^2$ and $2 \times 10^7 N/m^2$.

2. A process according to claim 1, wherein said aromatic hydrocarbon is benzene.

* * * * *